United States Patent [19]

Brailsford

[11] 4,077,263
[45] Mar. 7, 1978

[54] VACUUM OPERATED SAMPLER

[76] Inventor: Harrison D. Brailsford, 670 Milton Point Rd., Rye, N.Y. 10580

[21] Appl. No.: 710,709

[22] Filed: Aug. 2, 1976

Related U.S. Application Data

[63] Continuation of Ser. No. 600,211, Jul. 30, 1975, abandoned.

[51] Int. Cl.² ............................................. G01N 1/14
[52] U.S. Cl. ................................................. 73/421 B
[58] Field of Search ...................................... 73/421 B

[56] References Cited

U.S. PATENT DOCUMENTS

| | | | |
|---|---|---|---|
| 3,587,670 | 6/1971 | Brailsford | 73/421 B |
| 3,880,011 | 4/1975 | Johnson | 73/421 B |
| 3,901,084 | 8/1975 | Brailsford | 73/421 B |
| 3,901,087 | 8/1975 | Fabritus | 73/421 B |

Primary Examiner—S. Clement Swisher
Attorney, Agent, or Firm—Donald P. Gillette

[57] ABSTRACT

A vacuum pump controlled by a timer periodically evacuates a metering chamber to draw liquid samples into the chamber from a source. A switch is actuated when the liquid level reaches a predetermined point and causes the motor to stop. An electrically controlled valve is connected to the metering chamber above the level of the intake nozzle of the pump and is closed when the pump is operating and open when the pump is stopped, thereby allowing air to enter the upper part of the chamber to relieve the vacuum and allow the metered sample to flow out through an outlet tube to a sample receptacle. The outlet tube is controlled by a vacuum operated pinch valve to be closed during sample intake so that the pump will not have to evacuate the sample container before starting to draw liquid into the metering chamber.

9 Claims, 2 Drawing Figures

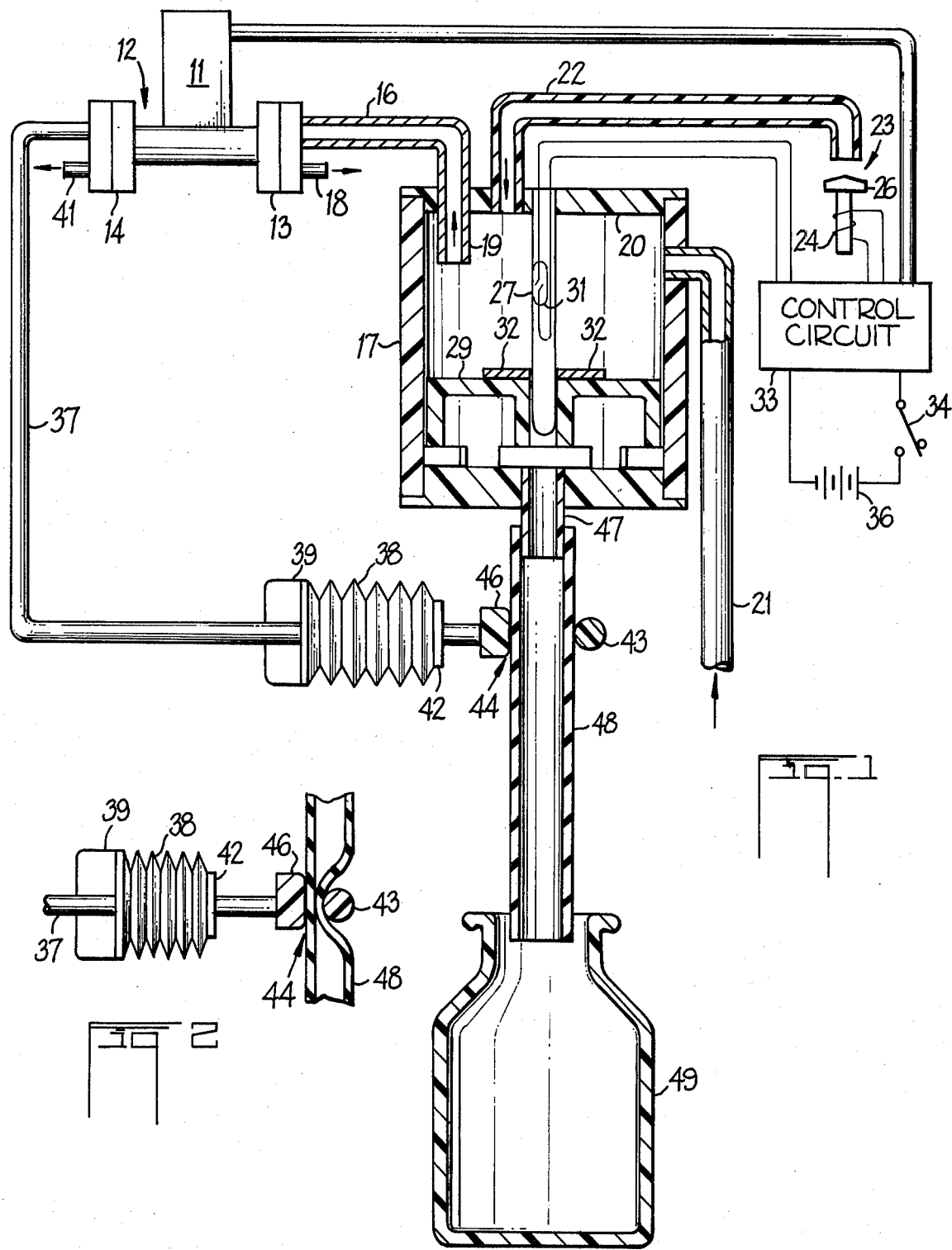

VACUUM OPERATED SAMPLER

This is a continuation of application Ser. No. 600,211, filed July 30, 1975 now abandoned.

BACKGROUND OF THE INVENTION

Field of the Invention

This invention relates to the field of vacuum-operated liquid sampling devices and particularly to apparatus for efficiently controlling the intake of samples into a metering chamber and automatically closing the outlet during the intake portion of each cycle.

The Prior Art

Gathering samples of liquid or gas at regular intervals or in regular quantities is necessary for many analytical purposes. It has become recognized as of increasing importance in the environmental field in recent years, for measuring of both water pollution and air pollution. The locations at which the samples must be gathered are often remote from any source of electric power, and as a result, the gathering apparatus must have its own self-contained power source, usually in the form of rechargeable batteries. Sample-gathering locations remote from regular sources of electric power are also likely to be physically inaccessible, so that the apparatus must be as light as possible, consistent with the need for reliability, to permit it to be carried to such locations as easily as possible. The load placed on the batteries by the apparatus must be low to result in good battery life and to permit lightweight batteries to be used, and the weight of other components must also be considered in the light of the same requirements.

The source from which samples are to be gathered, for example a stream or the atmosphere, may change from hour to hour, and refinements in analytical technique may require that the samples be gathered accordingly. In prior patents I have described means for gathering liquid samples by periodically evacuating a metering chamber to draw in samples of a selected size and then allowing the sample to flow out of the metering chamber into a sample receptacle or one of a group of separate receptacles.

One of the disadvantages of certain prior art apparatus, including apparatus described in some of my prior patents but not all of them, is that the sample receptacle, whether singular or plural, has been part of a closed system with the metering chamber and has had to be evacuated at the same time that the metering chamber was evacuated before a new liquid sample could be drawn into the metering chamber.

It is one of the objects of the present invention to provide sampling apparatus in which only the metering chamber need be evacuated to draw in a new sample.

It is another object of the present invention to avoid the necessity of providing a virtually vacuum-tight connection to the sample receptacle in liquid sampling apparatus.

A further object is to make more efficient use of the vacuum pump by requiring it to make operation of the apparatus relatively independent of the height of the metering chamber above the source being sampled.

These and other objects will be apparent from the following specification together with the drawings.

SUMMARY OF THE INVENTION

In the present invention, as in my prior inventions of sample-gathering apparatus, liquid samples are drawn from a source by means of a vacuum. The term "vacuum" is used herein with the understanding that it means a pressure low enough in comparison with the pressure of or on the source to draw the sample into a metering chamber. It is not to be understood as meaning an absolute vacuum. The vacuum is produced by a pump, preferably driven by a battery powered motor, which is connected to a metering chamber that has an intake tube that extends into the liquid source to be sampled. An outlet tube at the bottom of the metering chamber allows the liquid sample that has been drawn into the chamber to flow out when the pump stops. A flexible tube of rubber or similar, suitable, resilient material is connected to the outlet of the chamber and passes through the jaws of a vacuum-operated clamp that acts as a valve and is controlled by the vacuum pump to be closed during the time that the pump is in operation. The rubber tubing extends either directly into a sample receptacle or into a distributor or manifold connected to several sample receptacles.

A switch is located on or in the metering chamber to be actuated when the height of the liquid drawn into the chamber reaches a certain point. The switch may include any one of a variety of types. For example, the switch may simply consist of contacts to be short circuited by the liquid when the liquid reaches the predetermined level in the metering chamber. Or the switch may be magnetically-operated to be actuated by a magnet on a float lifted by the incoming liquid. Still another possible form of switch is a light-actuated switch actuated by interrupting or reflecting a light beam when the liquid reaches the predetermined height in the metering chamber. Still other forms of switch may be used.

The switch is connected to the motor that actuates the vacuum pump, and actuation of the switch causes the motor to stop running when the proper quantity of liquid has been drawn into the metering chamber. The connection between the switch and the pump motor may be direct or, preferably, by way of a timer that controls the length of time between successive operating periods of the pump.

An electrically-operated valve is also connected to the motor to control an air intake at the upper part of the metering chamber. While the motor is running, this valve is closed to facilitate evacuating the chamber. When the switch is actuated, the motor stops and the valve is deenergized to allow air to enter the chamber, thereby permitting the liquid sample to flow easily out of the chamber and into the sample receptacle. In order to protect the valve against inadvertent flooding in the event that the switch fails to function and therefore does not cause the pump to turn off, the intake nozzle of the pump is extended into the metering chamber to a level below the connection to the valve. If the switch does not turn the pump off, the liquid will be drawn into the pump and will stall the pump before the liquid can reach the valve.

BRIEF DESCRIPTION OF THE DRAWINGS

FIG. 1 is a front-elevational view of a liquid sampler constructed according to the invention.

FIG. 2 shows an alternative position of the outlet control valve during the sample intake portion of a complete operating cycle of the apparatus in FIG. 1.

DETAILED DESCRIPTION OF THE INVENTION

The sampler shown in FIG. 1 includes an electric motor 11, which is preferably a DC motor of the transistor-commutated type to provide efficient operation unattended over a long period of time. The motor 11 is connected to a vacuum pump 12, which in this case is a double-ended pump having two pumping sections 13 and 14 connected to the shaft of the motor 11. The section 13 is connected by an intake 16 to a metering chamber 17 and is provided with an exhaust tubing 18 through which air drawn from the chamber 17 can be exhausted to the atmosphere. It will be noted that the end of the tubing 16 extends as a nozzle 19 through the top 20 and a short distance into the metering chamber 17.

The metering chamber has an intake pipe 21 that extends down to the level of the liquid to be sampled. The vertical distance between the metering chamber 17 and the liquid to be sampled will vary from one location to another and in some instances a relatively long piece of tubing 21 may be required, subject, of course, to the well-known physical limitation on the height to which the liquid can be drawn by vacuum above its natural surface level. In other instances, the length of the tubing 21 may be as short as a few inches. Another tubing 22 is connected to the metering chamber through the top 20 so as to be above the lowest level of the nozzle 19. The tubing 22 leads to an electrically-operated valve 23 which includes a coil 24 and a closure member 26 that closes off the end of the tubing 22 when current flows through the coil 24.

A central guide rod 27 extends downwardly from the inner surface of the top 20 of the metering chamber 17, and a float 29 is guided by the rod so that it can slide up and down as the level of liquid in the metering chamber 17 changes. Near the upper end of the rod is a magnetic reed switch 31 located in the vicinity of the lowermost point of the nozzle section 19. More specifically, the position of the switch 31 is determined by a magnetic structure 32 attached to the float 29 to actuate the switch 31 when the float 29 is raised to a predetermined level by the liquid sample drawn into the chamber 17. The position of the magnetically actuated elements in the switch 31 is such that these elements are brought into contact with each other by the megnetic field of the structure 32 when the liquid sample is of the desired volume and the surface of the liquid is below the nozzle 19.

The motor 11, the coil 24, and the switch 31 are connected to a control circuit 33. The purpose of this circuit is to permit the closing of the switch 31 to interrupt the flow of the current through the motor 11, thereby stopping the motor and the pump 12. The control circuit 33 includes a timer, preferably a timing circuit that requires very little power. The timing circuit determines the length of an operating cycle of the apparatus, for example by determining the length of time that the motor 11 remains inoperative following actuation of the switch 31.

The vacuum pump 12 is shown as having two pumping sections, although it would be possible to use only one. The second section 14 is connected by a length of tubing 37 to a bellows 38 mounted on a fixed support 39. The pump section 14 has an exhaust tube 41 through which air from the bellows 38 is exhausted to the atmosphere. The free end 42 of the bellows 38 is connected to a movable member 43 of a valve 44. The member 43 is moved relative to a fixed member 46 by movement of the free end 42 of the bellows.

The metering chamber 17 has an outlet 47 to which a resilient tube 48 is connected. The tube 48 passes between the fixed member 46 and the movable member 43 to a sample receptacle 49.

It will be noted that the tube 48 is not connected by a vacuum-tight stopper to the receptacle, although it could be. It could also be connected to a distributor that, in turn, was connected to several sample receptacles. Such a distributor is shown in my co-pending patent application Ser. No. 490,057, filed July 19, 1974. One advantage of connecting the tube to vacuum-tight sample receptacle means is that, if the apparatus is left unattended too long, liquid will finally accumulate in the tube 48 and the chamber 17. The switch 31 will remain actuated, thereby keeping the motor 11 from running longer than the number of operating cycles necessary to fill the system.

If the tube 48 does not lead to a vacuum-tight sample receptacle system, it is necessary to provide the valve 44 to close off the outlet 47 so that the pump 12 can evacuate the chamber 17 to draw in a liquid sample. Even if the sample receptacle system is vacuum-tight, it is still desirable to provide the valve 44, because otherwise the pump 12 will have to evacuate the sample receptacle system along with the chamber 17 before liquid will be drawn into the chamber. This will avoid affecting the operation of the sampling apparatus differently for different heights of the apparatus above the source of liquid being sampled.

FIG. 2 shows the bellows 38 in its collapsed condition in response to operation of the vacuum pump 12. In this condition the movable member 43 is drawn firmly against the tube 48 to collapse the tube against the fixed member 46 and thereby close off the outlet 47.

When the motor 11 is turned off as a result of actuation of the switch 31, the pumping section 14 has enough built-in leakage to allow air to return to the bellows in time to release the pressure applied by the valve 44 to the tube 48. However, if faster release is desired, an orifice may be connected to the tubing 37. Such an orifice might be in the form of another valve similar to the valve 23.

Although the pumping section 13 would also provide some leakage to allow air to re-enter the chamber 17, it is desirable to have the valve 23 to allow air to re-enter more quickly. This facilitates purging the intake tubing 21 of liquid that has been drawn almost up to the point where it empties into the chamber 17. It also facilitates rapid passage of the liquid sample through the tube 48 to the sample receptacle 49. Rapid purging of the tubing 21 and rapid passing of the liquid through the tube 48 are desirable because of the nature of some of the liquids that may be sampled by the apparatus.

What is claimed is:
1. A liquid sampler comprising:
   A. a vacuum pump;
   B. a motor connected to operate said pump;
   C. a metering chamber;
   D. connection means connecting said chamber to said pump to be evacuated thereby;
   E. an inlet tube connected to said chamber to pass liquid from a source to said chamber when said chamber is evacuated;
   F. air inlet means for said chamber;

G. an outlet for said chamber to allow liquid in said chamber to drain into a sample receptacle;

H. a valve connected to said outlet to allow said liquid to flow therethrough when said valve is open and to prevent air from flowing therethrough when said valve is closed; and I. switching means responsive to the accumulation of a predetermined quantity of liquid in said chamber to stop said pump and allow said liquid to flow out of said chamber through said outlet.

2. The sampler of claim 1 in which said valve comprises valve-actuator means connected to said pump to be actuated thereby when said pump is running.

3. The sampler of claim 2 in which said outlet comprises a resilient tube and said valve-actuator means comprises means to pinch said resilient tube closed when said pump is running.

4. The sampler of claim 2 in which said pump comprises a first pumping section connected to said connection means to evacuate said chamber and a second pumping section connected to said valve-actuator means to close said valve simultaneously with but separately from evacuation of said chamber.

5. The sampler of claim 2 in which said valve-actuator means comprises a bellows.

6. The sampler of claim 1 in which said switch means is actuated when the liquid reaches a certain height in said chamber and said connection means extends into said chamber to a level between said certain height and said air inlet to prevent the liquid from accidentally rising into said air inlet.

7. The sampler of claim 6 comprising, in addition, a second valve connected to said air inlet to open and close it and connected to said switch means to be controlled thereby to open said air inlet when said pump is not running.

8. The sampler of claim 7 in which said second valve is electrically operated.

9. The sampler of claim 1 comprising, in addition, a timer connected to said motor to turn said motor on at predetermined intervals, said pump thereupon continuing to run until turned off by said switch.

* * * * *